US00PP11746P2

(12) United States Plant Patent
Sanford et al.

(10) Patent No.: US PP11,746 P2
(45) Date of Patent: Jan. 23, 2001

(54) RED RASPBERRY PLANT NAMED 'ENCORE'

(75) Inventors: John C. Sanford, Geneva; Kevin E. Maloney, Phelps; Jack E. Reich, Geneva, all of NY (US); Donald K. Ourecky, Fort Lauderdale, FL (US)

(73) Assignee: Cornell Research Foundation, Inc., Ithaca, NY (US)

( * ) Notice: Under 35 U.S.C. 154(b), the term of this patent shall be extended for 0 days.

(21) Appl. No.: 09/166,855

(22) Filed: Oct. 6, 1998

(51) Int. Cl.[7] ..... A01H 5/00
(52) U.S. Cl. ..... Plt./204
(58) Field of Search ..... Plt./204

(56) References Cited

U.S. PATENT DOCUMENTS

P.P. 5,404 * 2/1985 Sanford et al. ..... Plt./204
P.P. 10,610 * 9/1998 Swartz et al. ..... Plt./204

OTHER PUBLICATIONS

Program and Abstracts Seventh International Rubus–Ribes Symposium Australia and New Zealand, Jan. 9–16, 1998, title page and p. 7.

Proceedings 1998 Pennsylvania Vegetable Conference and Trade Show, Hershey, PA, presentation Jan. 28, 1998, title page, pp. 3 and 45.

1998 New York State Vegetable Conference and Berry Growers Meeting Feb. 10–12, Proceedings, title pages, table of contents, pp. 7, 8, 9.

New York Berry Grower, Apr. 1998, pp. 1 and 7.

New York Berry Grower, Dec. 1997, pp. 1, 10 and 11.

News Releases by Department of Communications, NYSAES, Geneva, New York, on Feb. 10, 1998, pp. 1 and 4.

Cornell University Station News, vol. LXXIX, No. 6, Feb. 13–20, 1998, NYSAES, Geneva, New York, p. 1.

CALS News (monthly newsletter of College of Agriculture and Life Sciences) of Cornell University, vol. 4–6, Mar. 1998, pp. 1 and 2.

New York's Food and Life Sciences Bulletin, No. 152, Jan., 1998.

* cited by examiner

*Primary Examiner*—Bruce R. Campell
*Assistant Examiner*—Wendy A Baker

(57) ABSTRACT

A new and distinct cultivar of red raspberry plant named 'Encore' matures a high percentage of fruit from late July to early August in the East Coast and Great Lakes regions, thereby extending the summer harvest season and decreasing the gap between the summer and fall harvest seasons.

13 Drawing Sheets

The invention was made in part with Federal formula funds pursuant to the Hatch Act and was part of Project 632-496. The United States Government has certain rights in the invention.

BACKGROUND OF THE INVENTION

In the East Coast and Great Lakes regions, summer red raspberry harvest generally peaks in mid-July creating a considerable gap prior to harvest of primocane fruiting raspberries in mid-August. Providing a red raspberry plant which matures a high percentage of fruit from late July to early August in said regions, would have the benefit of decreasing the gap between summer and fall harvest seasons.

SUMMARY OF THE INVENTION

This invention relates to a new and distinct cultivar of red raspberry plant, named 'Encore,' that matures a high percentage of fruit from late July to early August in the East Coast and Great Lakes regions, thereby extending the summer harvest season and decreasing the gap between the summer and fall harvest seasons. It provides commercial yields of large size fruit from late July to early August in said regions. It has been consistent in its performance over many years of testing. It has consistently expressed good winter hardiness, optimum vigor, and superior fruit size and fruit yields on an annual basis.

'Encore' plants are winter hardy in zone 5 and are vigorous. Vigor is above average when compared to standard cultivars.

The leaves are dark green when mature and healthy and have a coarse upper surface with noticeable ridges. The leaf serrations are larger than those of 'Taylor' (unpatented) red raspberry plant leaves but the leaf edges are not notched like those of 'Tulameen' (unpatented) red raspberry plants. The leaf serrations are not as distinctly pointed as those of 'Titan' (patented as N.Y. 883, U.S. Plant Pat. No. P.P. 5,404) red raspberry plants. The leaves have moderate hair density on the upper leaf surface. The hairs are shorter and present in less density than the hairs on leaves of 'Titan' (unpatented) red raspberry plants and they are more widely distributed than the hairs on leaves of 'Taylor' red raspberry plants.

Actively growing terminals on primocanes have a light green color.

The color of newly expanded primocane leaves of 'Encore' is most similar to Yellow Green 145—Group A compared to Yellow Green 149—Group A for 'Heritage', Green 141—Group C for 'Titan', and Green 140—Group A for 'Taylor'. These color codes correspond to those in The Royal Horticultural Society Color Chart, London.

The canes of the 'Encore' raspberry plant are nearly spineless, are sturdy and do not require trellising. A very few short spines which point downwardly are present on the dormant cane base, and the cane base color is different from that of 'K8106' (unpatented), 'Titan,' 'Taylor' and 'Canby' (unpatented) red raspberry plants. The tip of the dormant cane of 'Encore' red raspberry plants is spineless whereas this is not the case for K81-6, 'Titan' and 'Taylor' red raspberry plants, and the color of the dormant cane tip of 'Encore' is different from that of the dormant cane tip of 'Canby' and K81-6 red raspberry plants.

Root suckering is above average, when compared to standard cultivars.

'Encore' fruit are attractive, large in size with firm texture and have a good balanced flavor.

'Encore' red raspberry plants are more productive, larger fruited and later maturing than the late maturing 'Taylor' red raspberry cultivar.

'Encore' red raspberry plants are distinctly later maturing, have similar fruit size, are only slightly less productive and are less susceptible to Phytophthora, compared to the late maturing 'Titan' cultivar.

DETAILED DESCRIPTION

The 'Encore' plant is a new red raspberry plant developed by Cornell University at the New York State Agricultural Experiment Station in Geneva, N.Y. The 'Encore' cultivar originated from the cross 'Canby'×'Cherokee.' (unpatented) 'Canby' was selected from a cross of 'Viking' (unpatented)× 'Lloyd George' (unpatented) and was introduced in 1953 by the Oregon Agricultural Experiment Station. 'Cherokee' ['Hilton' (unpatented)×('Taylor'×'St. Regis' (unpatented))] was introduced in 1973 by Virginia Polytechnic Institute, Blacksburg, Va. The original cross was made in 1976 by the small fruit breeding program in Geneva, N.Y. 'Encore' was selected in 1980 from a seedling population of 206 progeny from this family. The 'Encore' selection was a single plant. The 'Encore' plant has undergone field testing at five sites in Geneva, N.Y. since 1977. 'Encore' has been asexually propagated utilizing tissue culture techniques, specifically, meristem culture and multiplication with the original explant material being meristems excised from dormant buds in primocane leaf axils, and root sucker propagation at Nourse Farms, Inc., 41 River Road, South Deerfield, Mass. 01373. Scientists and licensed evaluators have tested several thousand propagules. The plants have remained stable and true to type. The 'Encore' plant was previously known and tested at NY7.

Figure 1:
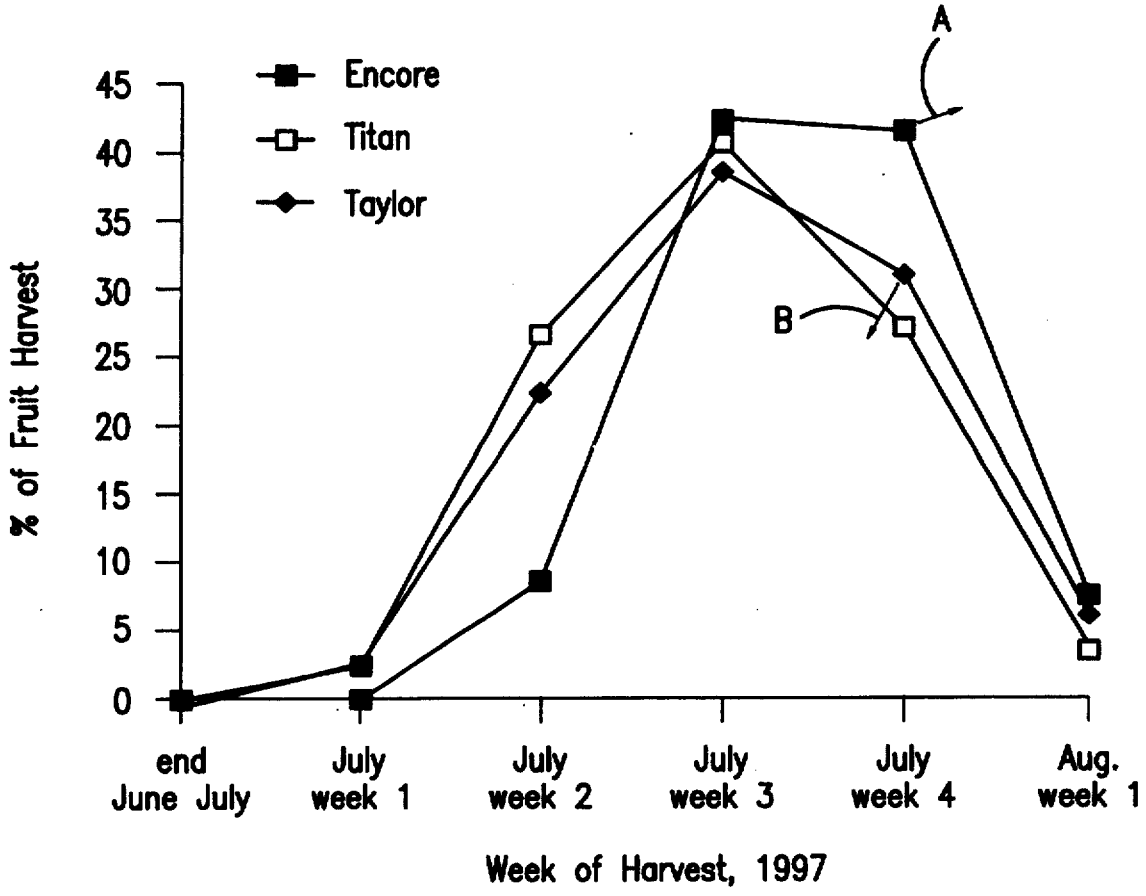
FIG. 1 depicts graphs showing percentage of total crop maturing for weeks from the end of June to the first week of August for 'Encore' red raspberry plants and two other late maturing red raspberry cultivars adapted to the East Coast and Great Lakes regions.

FIG. 1 compares the fruit maturities of 'Encore', 'Titan' and 'Taylor' red raspberry plants for summer harvesting in 1997. 'Titan' and 'Taylor' are standard late maturing red raspberry cultivars for the East Coast and Great Lakes regions. FIG. 1 shows that 'Encore' red raspberry plants matured 49% of their total crop in Geneva, N.Y. after July 27 as denoted by reference letter A; this 49% averaged 2.5 grams/berry. FIG. 1 shows that 'Taylor' red raspberry plants matured 36% of their total crop in Geneva, N.Y. after July 27 as denoted by reference letter B; this 36% averaged 1.8 grams/berry. FIG. 1 shows that 'Encore' raspberry plants are later maturing than 'Titan' raspberry plants. The average harvest period over four years (1994–1997)) at the Robbins Research Farm, located on Sutton Road in Geneva, N.Y., for 'Encore' red raspberry plants was July 13 to August 6. During these years, 'Encore' red raspberry plants on average matured 46% of their crop after July 23, and the average fruit size was 2.9 grams per berry. At the Robbins Research Farm in 1997, 'Taylor' red raspberry plants had similar maturity compared with 'Encore' red raspberry plants but had 53% lower yields and average berry size was 88% smaller. The average harvest season for 'Encore' raspberry plants at Darrow Farm, located on Gates Road in Geneva, N.Y., was July 11 to August 7 over the two periods 1996 and 1997. During this period, 'Encore' red raspberry plants matured 52% of their crop after July 23 and the average fruit size after July 23 was 2.9 grams per berry. At the Darrow Farm, 'Taylor' red raspberry plants matured 47% of their crop after July 23, the average fruit size after July 23 was 1.9 grams per berry and the total fruit yield was 12% less than for the 'Encore' raspberry plants.

Under heavy crop loads, 'Encore' cultivar produces adequate numbers of suckers to maintain high annual yields but without the need for heavy cane thinning during the dormant season.

Figure 3:
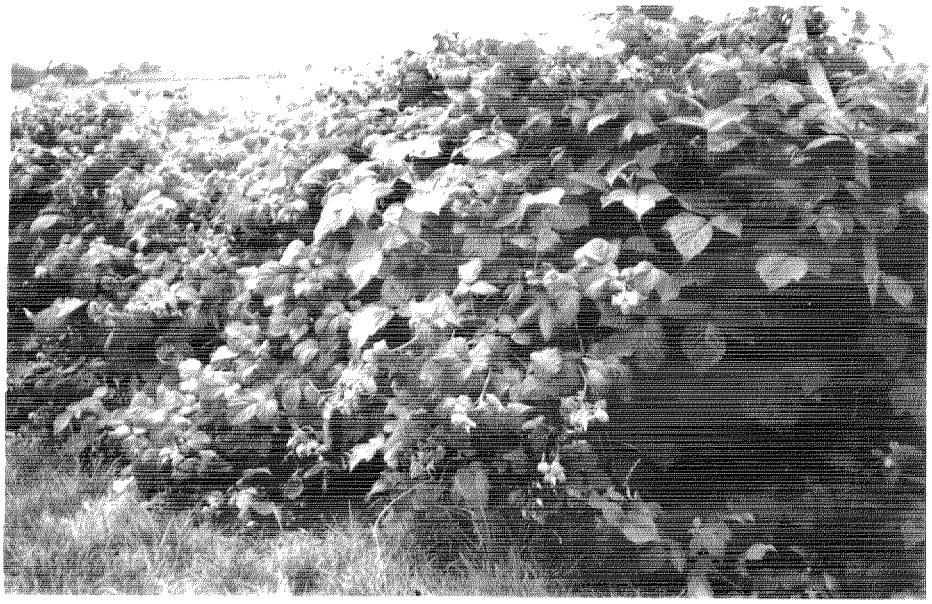
FIG. 3 is a photograph of a typical row of canes of 'Encore' raspberry plants in the field.

FIG. 3 shows the sturdy nature of the canes. While the canes do not require trellising, they are very productive and have long fruiting laterals which benefit from trellis support to improve harvest efficiency. 'Encore' averages nine new primocanes per crown each year. The diameter of the primocanes at the base averages 0.8 cm and 0.6 cm at the middle third. The floricane diameter at the base averages 1.1 cm and 1.0 cm at the middle third. Average bud break/shoot emergency date for 'Encore' is April 7 in Geneva, N.Y. The average internode distance is 2.5 cm for primocanes and 4.75 cm for floricanes. The primocanes average 78 cm in length. The floricanes average 140 cm in length.

Figure 6:
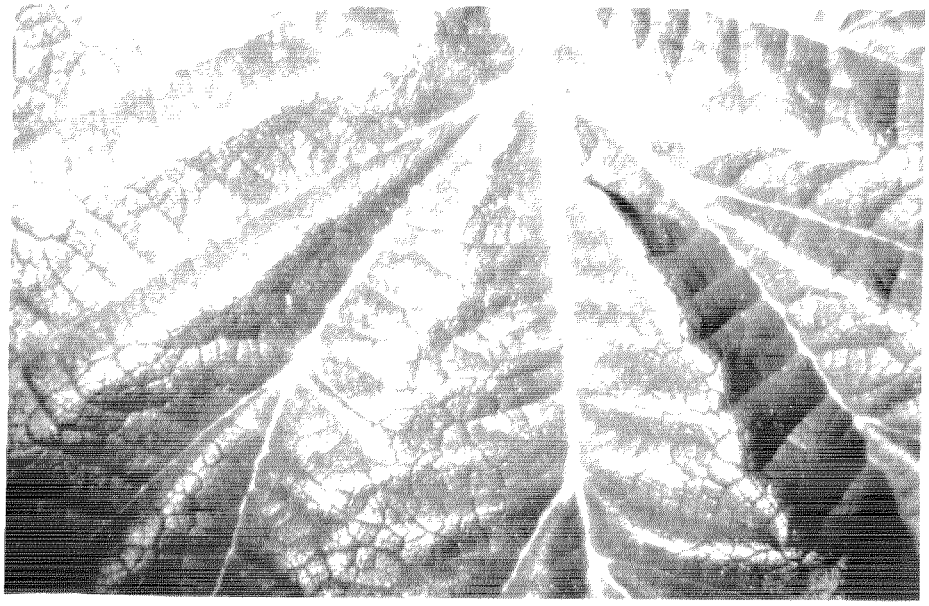
FIG. 6 is a photograph of the upper surface of a leaf of an 'Encore' red raspberry plant.
Figure 11:
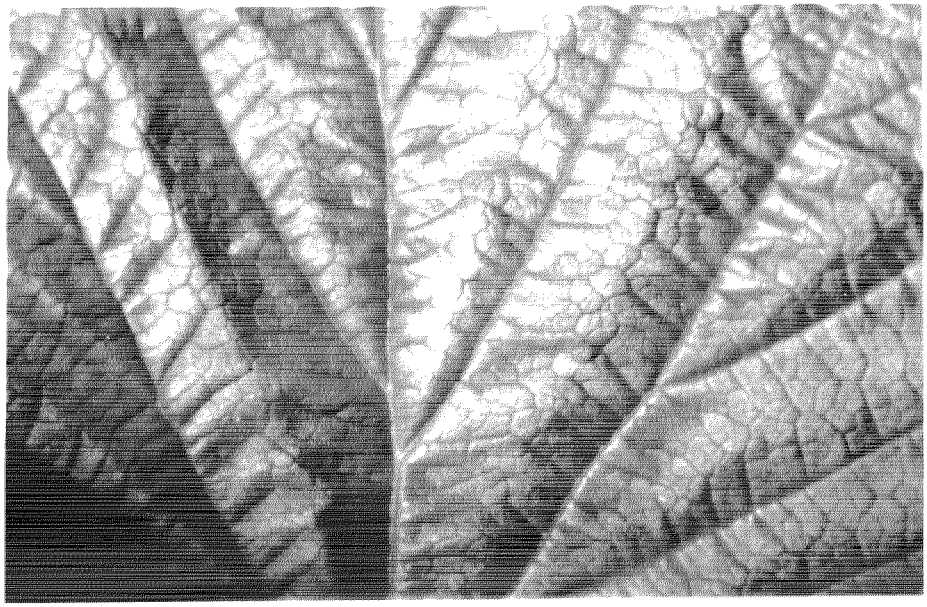
FIG. 11 is a photograph of the upper surface of a leaf of a 'Tulameen' red raspberry plant.

FIG. 6 shows the coarse upper leaf surface with noticeable ridges, of an 'Encore' raspberry plant. This contrasts with the more detailed upper leaf surface of a 'Taylor' red raspberry plant shown in FIG. 7 and of a 'Tulameen' red raspberry plant shown in FIG. 11.

Figure 8:
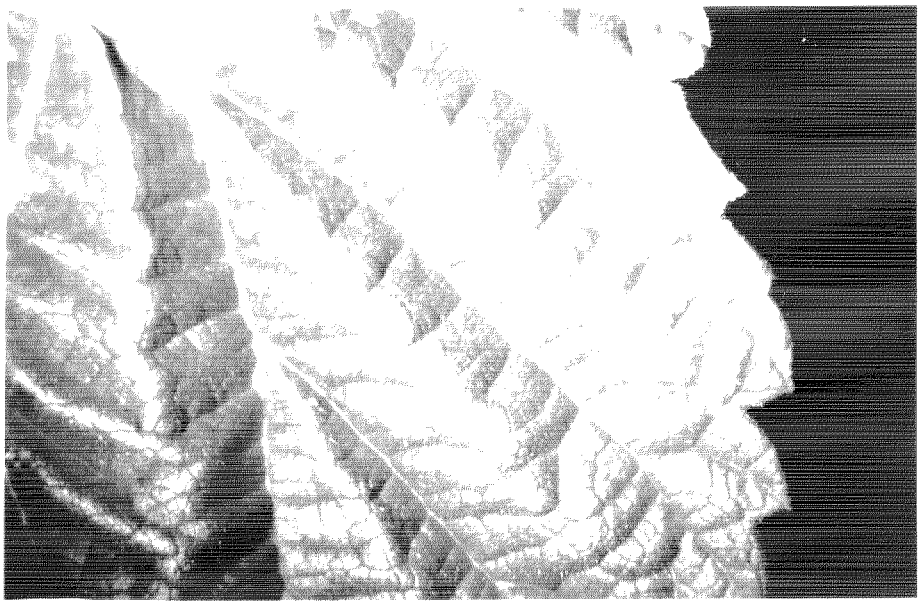
FIG. 8 is a photograph showing the edge serrations of a leaf of an 'Encore' red raspberry plant.
Figure 9:
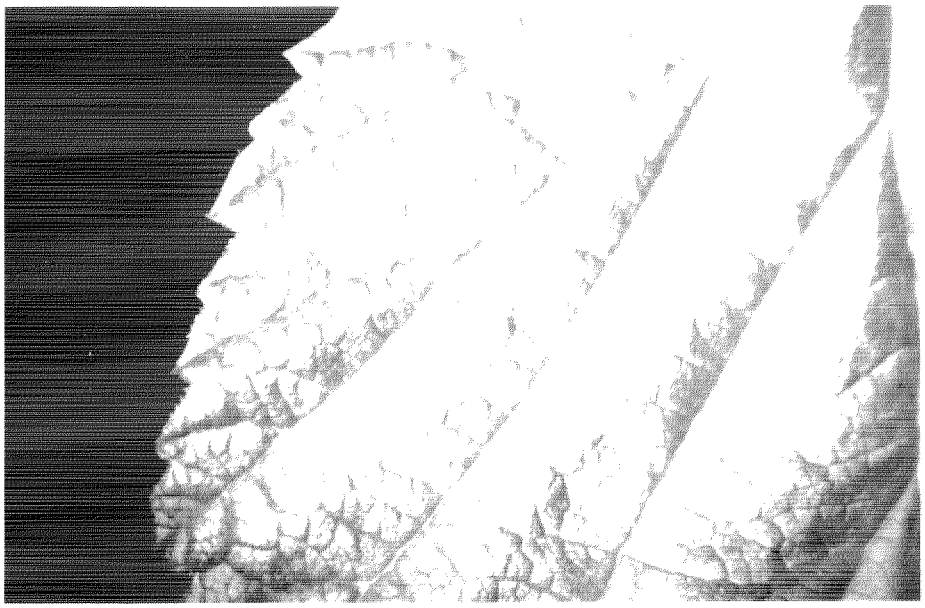
FIG. 9 is a photograph showing the edge serrations of a leaf of a 'Taylor' red raspberry plant.
Figure 10:
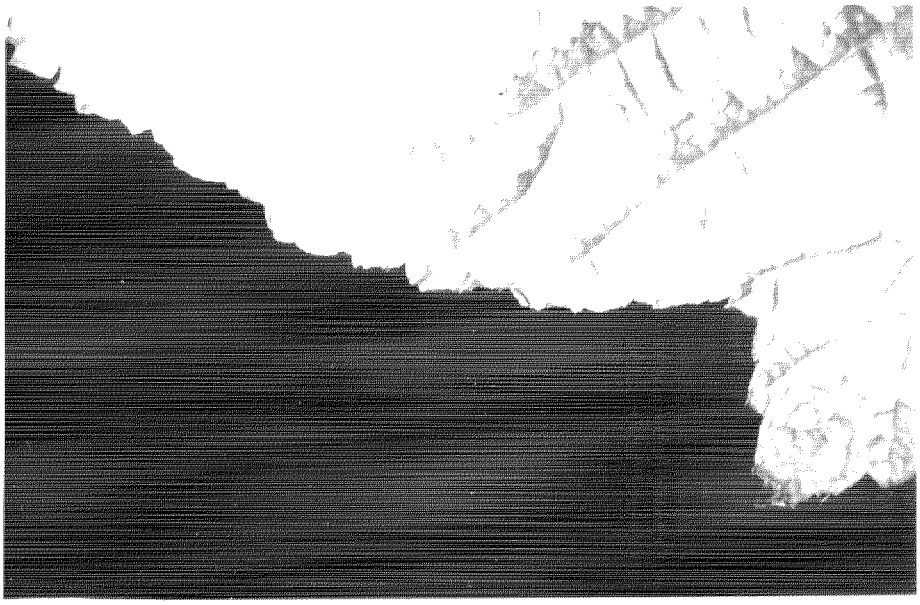
FIG. 10 is a photograph of the edge of a leaf of a 'Tulameen' red raspberry plant.

FIG. 8 shows the leaf edge serrations of an 'Encore' red raspberry plant. These leaf edge serrations are larger than the leaf edge serrations of a 'Taylor' red raspberry plant (shown in FIG. 9) but the leaf edges are not notched like those of a 'Tulameen' red raspberry plant (shown in FIG. 10). The leaf serrations are not as distinctly pointed as those of a 'Titan' red raspberry plant (shown in FIG. 15).

Figure 12:
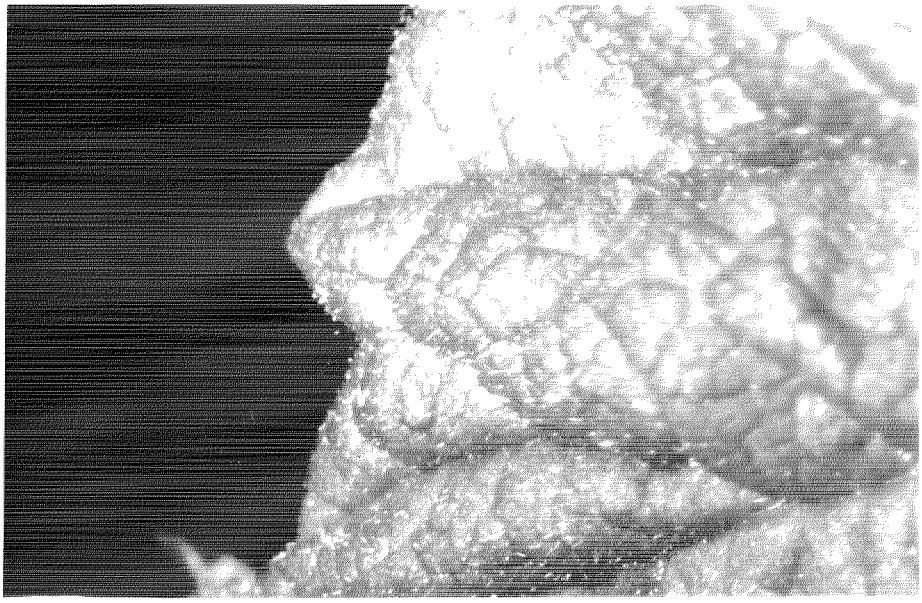
FIG. 12 is a photograph of the upper surface of leaf of an 'Encore' red raspberry plant with magnification sufficient to show the hairs thereon.
Figure 13:
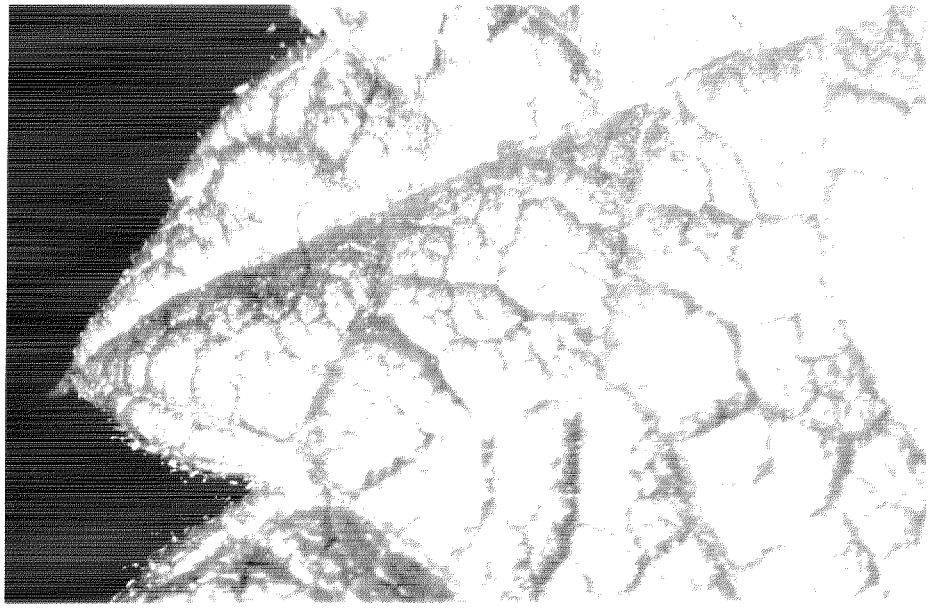
FIG. 13 is a photograph of the upper surface of leaf of a 'Taylor' red raspberry plant with magnification sufficient to show the hairs thereon.
Figure 15:
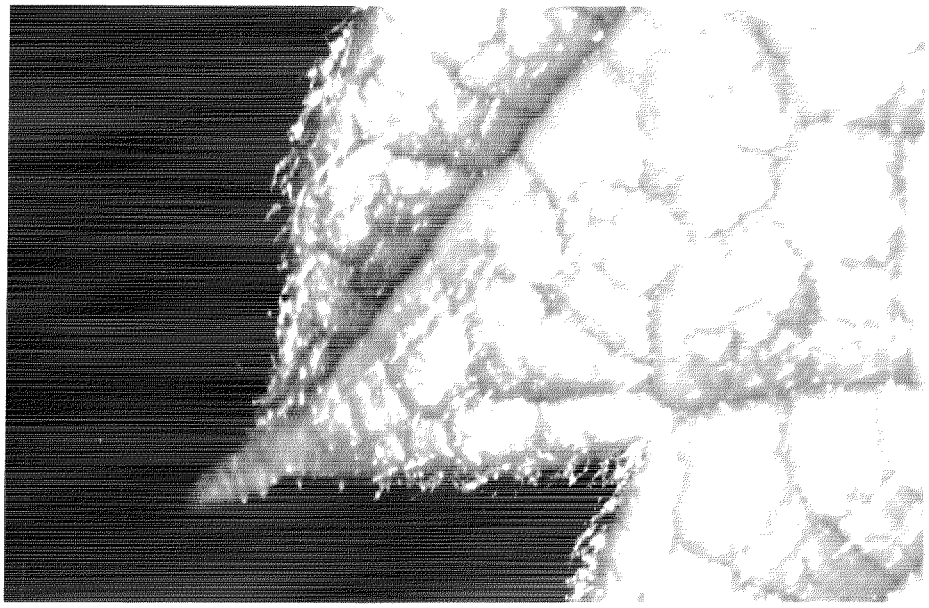
FIG. 15 is a photograph of upper leaf surface and leaf edge of a 'Titan' red raspberry plant with magnification sufficient to show the hairs thereon.

As shown in FIG. 12, the upper leaf surface of an 'Encore' red raspberry plant has a moderate hair density (pubescence) with few hairs on the leaf edge. On the other hand, as shown in FIG. 13, the upper leaf surface of a 'Taylor' red raspberry plant has very few hairs but contains hairs on the leaf edge. The hairs (pubescence) on upper leaf surface and leaf edges of a 'Titan' red raspberry plant are longer (as shown in FIG. 15) than the hairs on upper leaf surface of an 'Encore' red raspberry plant (as shown in FIG. 12).

Figure 7:
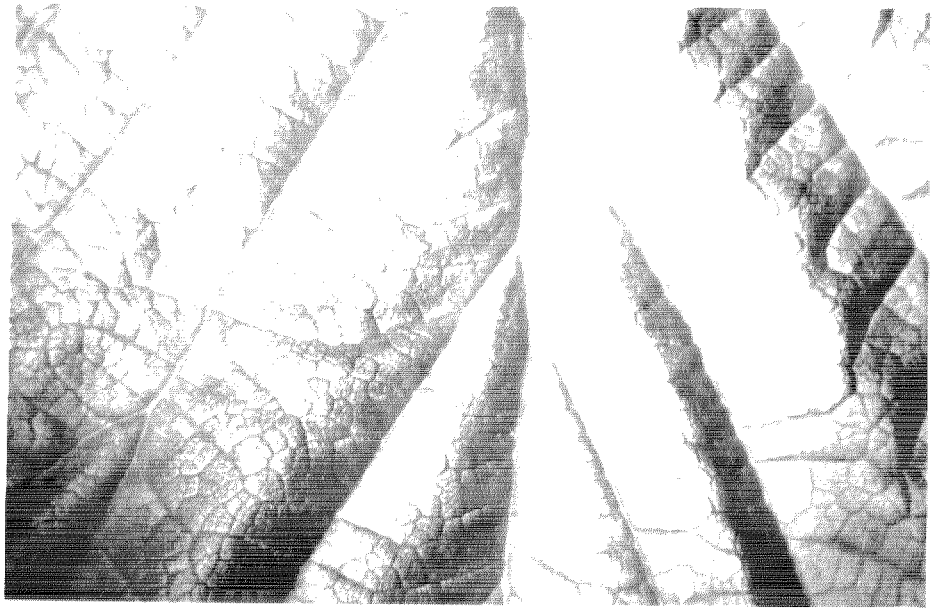
FIG. 7 is a photograph of the upper surface of a leaf of a 'Taylor' red raspberry plant.

While FIG. 6 directed to 'Encore' displays anthocyanin coloration and FIG. 7 directed to 'Taylor' displays little, if any, anthocyanin coloration and while FIG. 12 directed to 'Encore' displays no anthocyanin coloration and FIG. 13 directed to 'Taylor' displays anthocyanin coloration, the figures are labeled correctly. The pictures are not for characterization of leaf color but rather only for characterization of leaf texture and pubescence. Color in the leaves is variable depending on the age of the leaf. Also, pigmentation can be induced by damage from wind, sun, insects, or other causes so that only leaves of the same physiological age and position can be compared for pigment characteristics. The pictures of FIGS. 6 and 12 do not display leaves of the same physiological age and position. The pictures of FIGS. 7 and 13 do display leaves of the same physiological age and position.

The leaf arrangement for 'Encore' is compound with three leaflets. The rachis averages 4.5 cm in length, and the petiole on the terminal leaflet averages 1.7 cm. The lateral leaflets do not have petioles. There are two stipules present and the leaf cross-section is convex. The terminal leaflet on 'Encore' averages 7 cm in length and 5.75 cm in width. It is ovate in shape with an acuminate tip and an obtuse base. The margin is doubly serrate. The green color varies with age and season but fully expanded spring growth is most like Green 141—Group A. The lateral leaflets on 'Encore' average 5.25 cm in length and 4 cm in width with no overlap in mature leaves. Their orientation is digitate. They are ovate in shape with an acuminate tip and an obtuse base. Their margin is doubly serrate. The color varies with the age and health of the leaf, but fully expanded spring growth is most like Green 141—Group A.

We turn now to the dormant canes.

Figure 16:
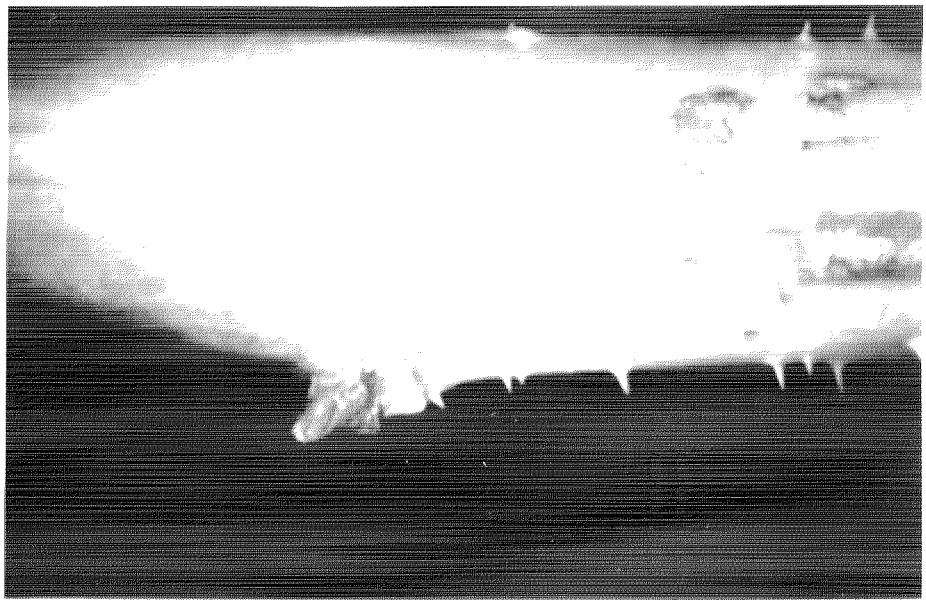
FIG. 16 is a photograph of the base of the dormant cane of an 'Encore' red raspberry plant.
Figure 17:
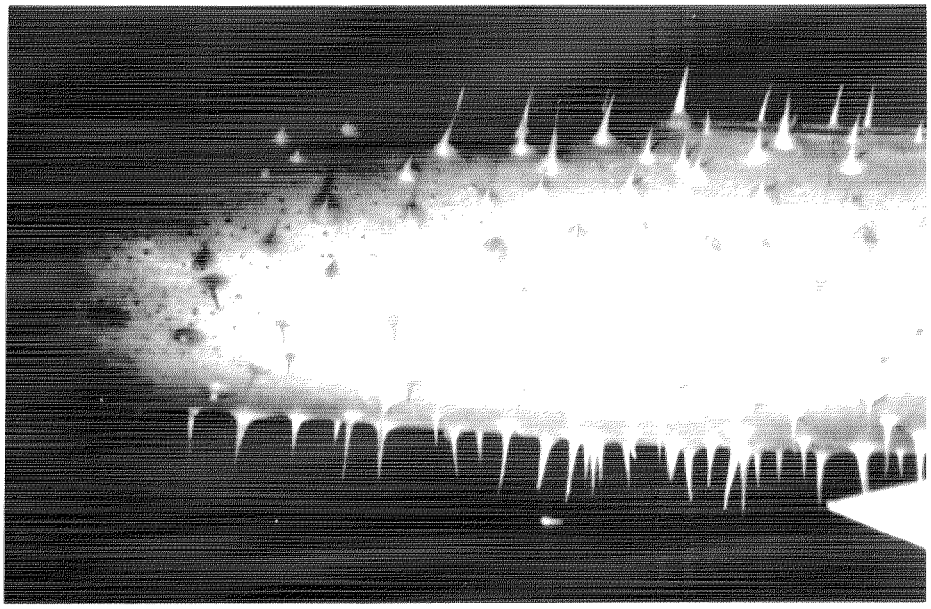
FIG. 17 is a photograph of the base of the dormant cane of a K81-6 red raspberry plant.
Figure 18:
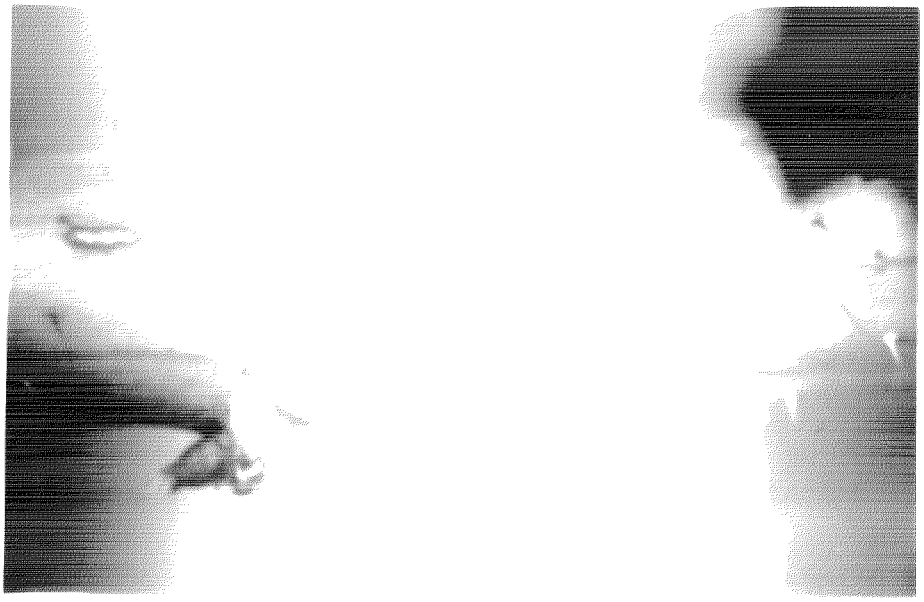
FIG. 18 is a photograph of the base of a dormant cane of a 'Titan' red raspberry plant.
Figure 19:
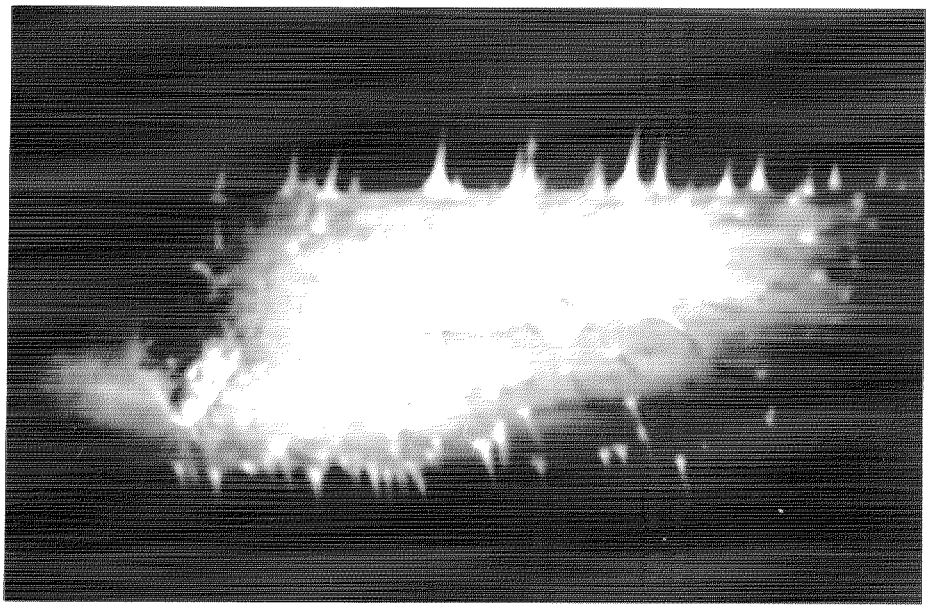
FIG. 19 is a photograph of the base of a dormant cane of a 'Taylor' red raspberry plant.
Figure 20:
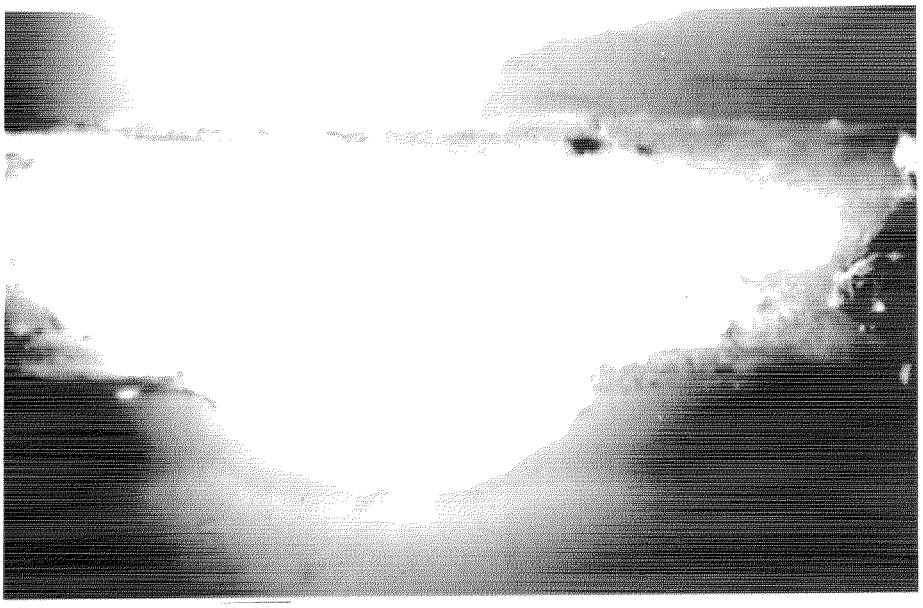
FIG. 20 is a photograph of the base of a dormant cane of a 'Canby' red raspberry plant.

FIG. 16 shows a dormant cane base of an 'Encore' red raspberry plant. As shown in FIG. 16, very few short spines are present which point downwardly. The dormant cane base color is most similar to Greyed-Orange 164—Group B. This color code and the others hereinafter corresponds to those in The Royal Horticultural Society Colour Chart, London. While the colors depicted in the attached photographic illustrations are as accurate as it is reasonably possible to obtain in an illustration of this character, the color chart colors listed in the specification should be considered to be accurate and controlling. In comparison, as shown in FIG. 17, a dormant cane base of a K81-6 red raspberry plant contains a dense concentration of long spines which point slightly downwardly and the color of a dormant cane base of a K81-6 red raspberry plant is similar to Greyed-Orange 165—Group B. In further comparison, as shown in FIG. 18, a dormant cane base of a 'Titan' red raspberry plant contains a sparse number of spines which are long and thin shaped and point slightly downwardly and the color of a dormant cane base of a 'Titan' red raspberry plant is similar to Greyed-Orange 165—Group B. In further comparison, as shown in FIG. 19, a dormant cane base of a 'Taylor' red raspberry plant has a dense concentration of spines which are long and point slightly downwardly and has a color similar to Greyed-Orange 165—Group C. In still further comparison, as shown in FIG. 20, a dormant cane base of a 'Canby' red raspberry plant is nearly spineless and has a color similar to Greyed-Yellow 161—Group C.

Figure 21:
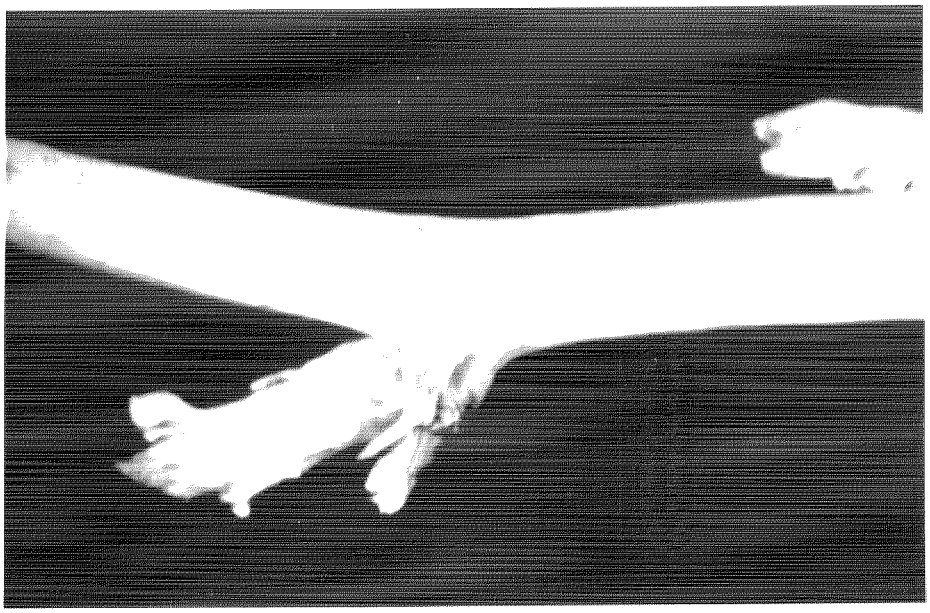
FIG. 21 is a photograph of the tip of a dormant cane of a 'Canby' red raspberry plant.
Figure 22:
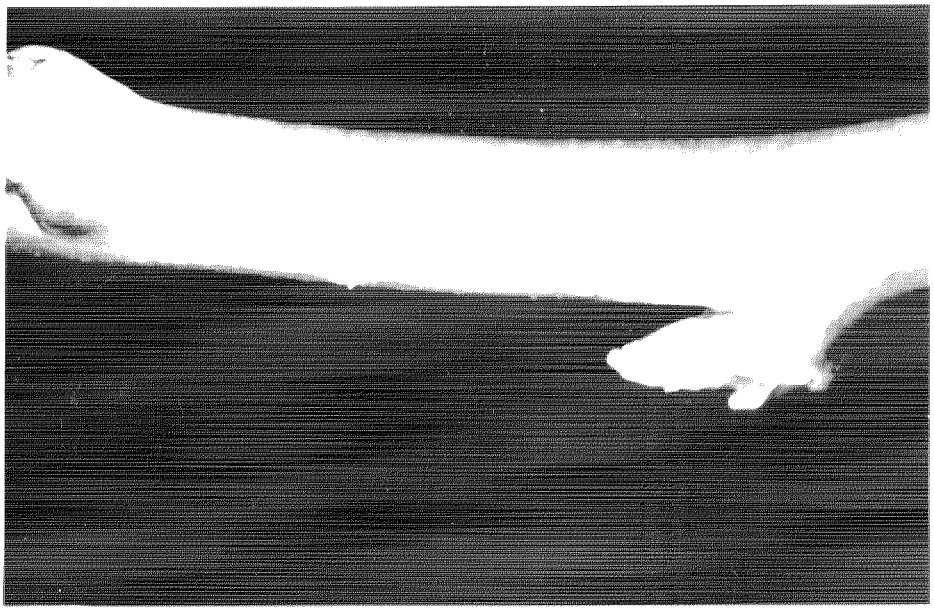
FIG. 22 is a photograph of the tip of a dormant cane of an 'Encore' red raspberry plant.
Figure 23:
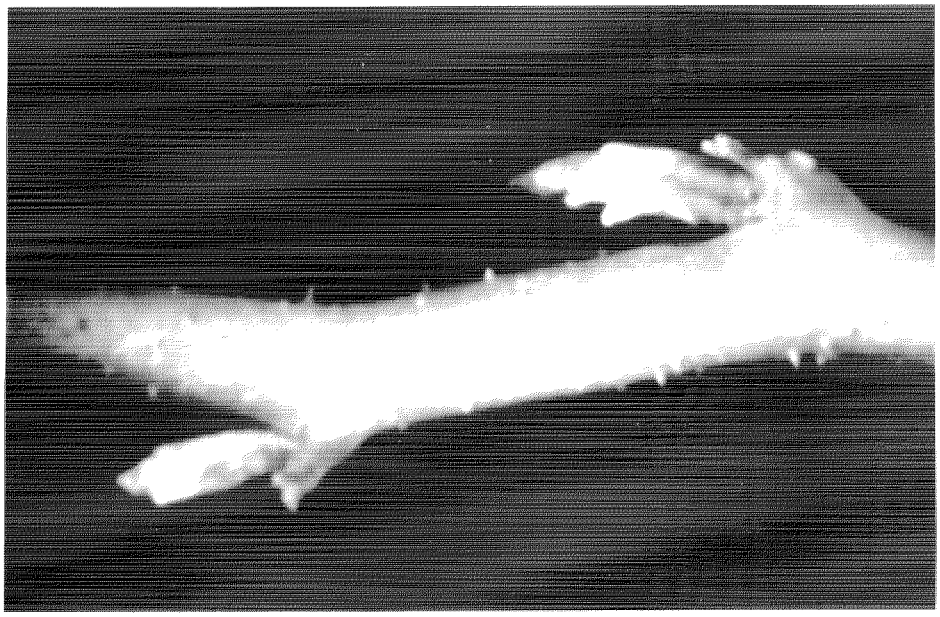
FIG. 23 is a photograph of the tip of a dormant cane of a K81-6 red raspberry plant.
Figure 24:
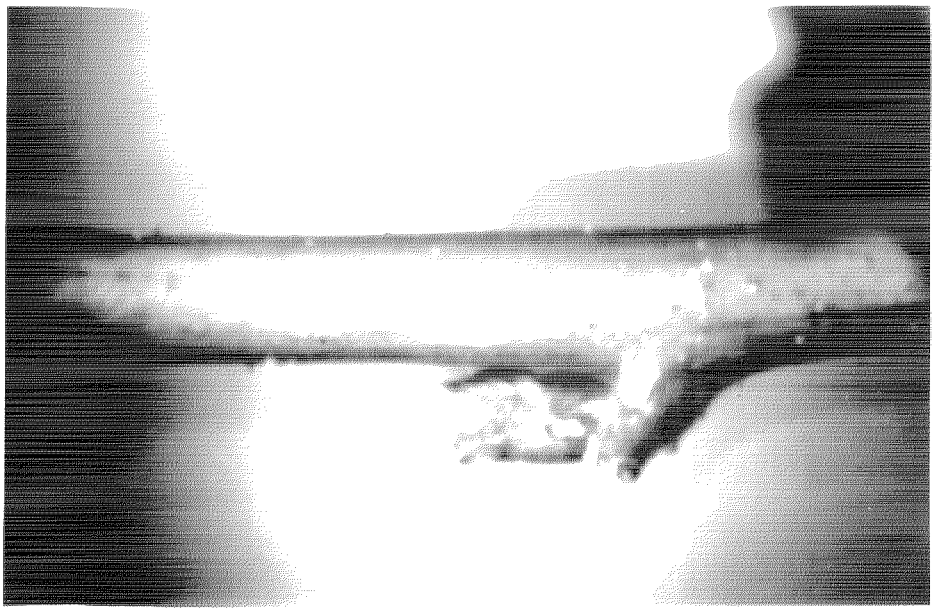
FIG. 24 is a photograph of the tip of a dormant cane of a 'Titan' red raspberry plant.
Figure 25:
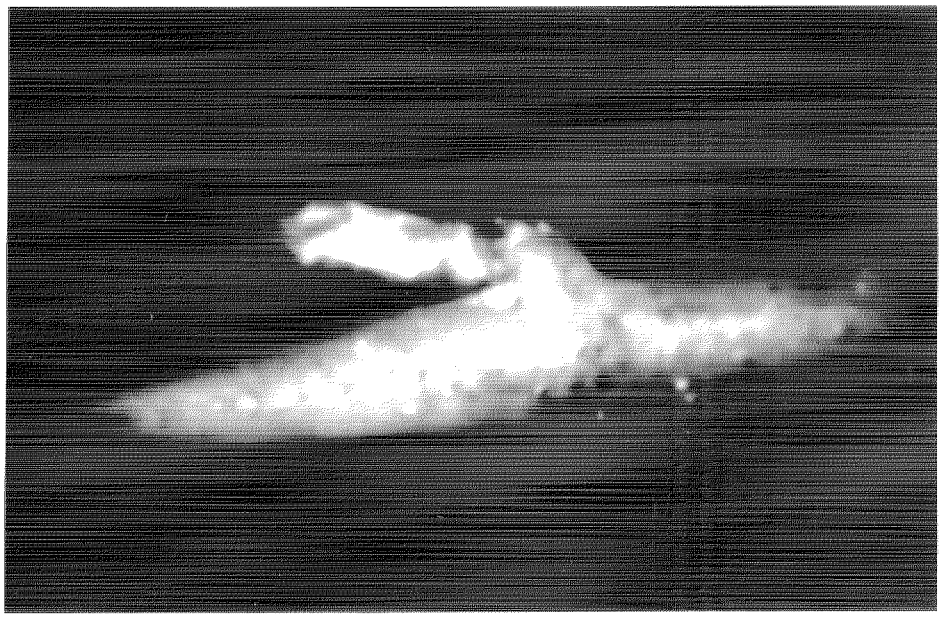
FIG. 25 is a photograph of the tip of a dormant cane of a 'Taylor' red raspberry plant.

FIG. 22 shows a dormant cane tip of an 'Encore' red raspberry plant. As shown in FIG. 22, the dormant cane tip of an 'Encore' red raspberry plant is spineless and the color of the dormant cane tip is most similar to Greyed-Orange 166—Group A. In comparison, as shown in FIG. 21, a dormant cane tip of a 'Canby' red raspberry plant is spine free and light in color with the color of the dormant cane tip being similar to Greyed-Orange 164—Group B. In further comparison, as shown in FIG. 23, a dormant cane tip of a K81-6 red raspberry plant has spines present in low density which point slightly downwardly and has a color similar to Greyed-Orange 177—Group E. In still further comparison, as shown in FIG. 24, a dormant cane tip of a 'Titan' red raspberry plant has spines present in low density which are blunt in shape and has a color similar to Greyed-Orange 166—Group A. In still further comparison, as shown in FIG. 25, a dormant cane tip of a 'Taylor' red raspberry plant has spines present in low density which are blunt in shape and has a color similar to Greyed-Orange 166—Group A.

'Encore' averages seven nodes per fruiting lateral on floricanes with an average of 1.5 flowers per node. The flowers on 'Encore' are rosaceous and actinomorphic in shape with five elliptic shaped petals. They average 1 cm in diameter with an average of 7.5 flowers per cluster. The pedicels average 2 cm in length. The pedicel color most resembles Yellow-Green 146—Group A with overtones of Red 47—Group A. The petal color most resembles Yellow-White 158—Group D.

'Encore' berries are conic in shape whereas 'Cherokee' berries are round-conic in shape. The fruit width of 'Encore' averages 2.5 cm and the fruit length of 'Encore' averages 3 cm. The number of druplets averages 102 per fruit. The fruit is firmer than the fruit of 'Reveille' (unpatented) and 'Lauren' (U.S. Plant Pat. No. 10,610).

Figure 2:
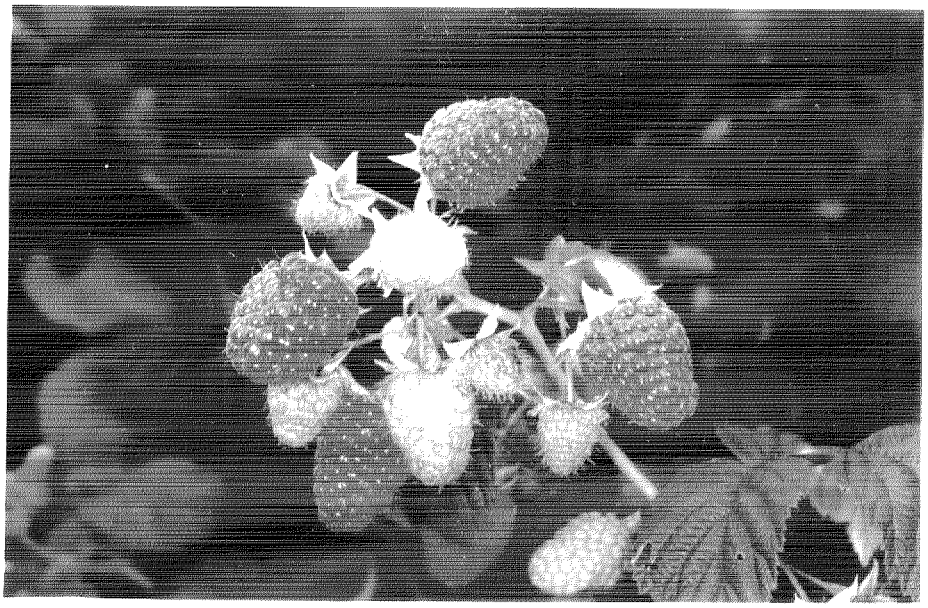
FIG. 2 is a photograph of a typical fruit cluster of an 'Encore' red raspberry plant in the field.
Figure 4:
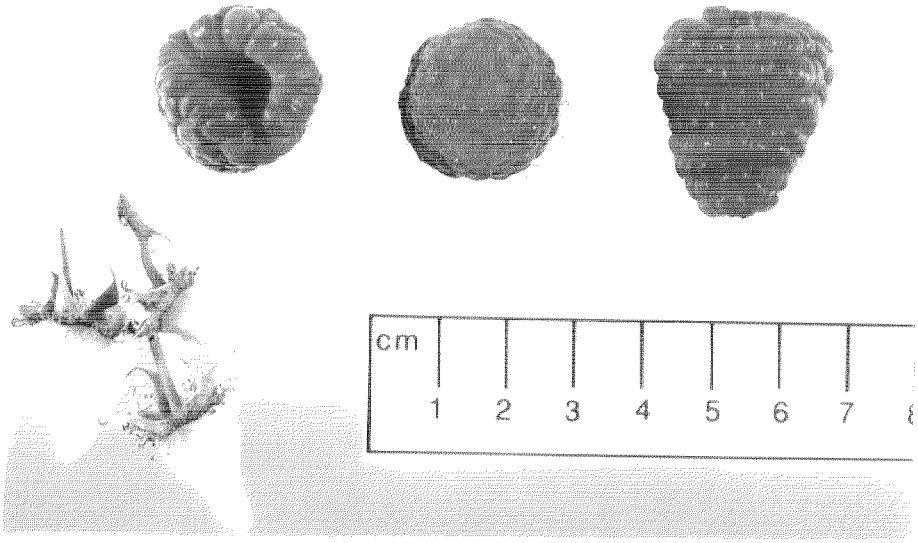
FIG. 4 is a photograph showing the size of fruit and receptacles of 'Encore' red raspberry plants.
Figure 5:
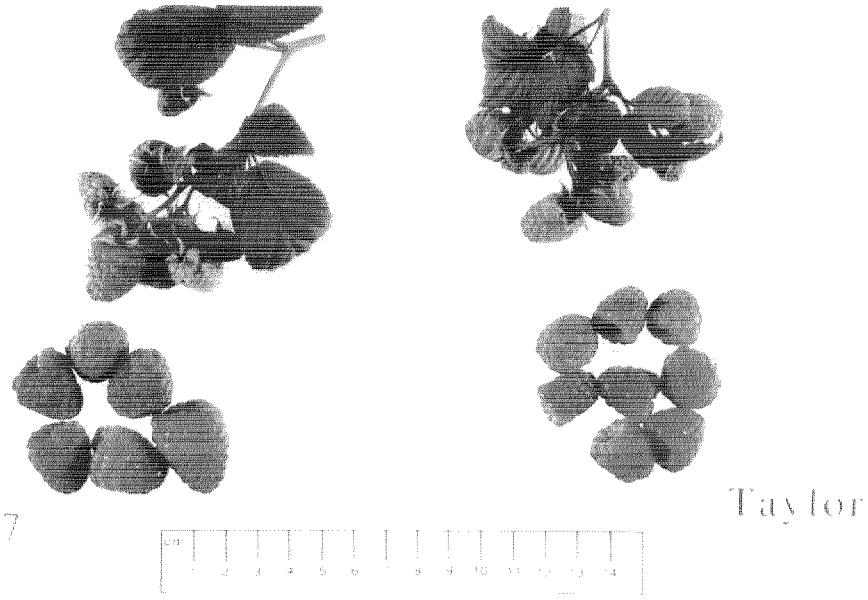
FIG. 5 is a photograph providing a size comparison of fruit of 'Encore' (NY7) and 'Taylor' red raspberry plants.

FIG. 2 depicts a typical fruit cluster of an 'Encore' red raspberry plant in the field. FIG. 4 shows the large size of the fruit of an 'Encore' red raspberry plant. FIG. 5 provides comparison of the size of fruit of an 'Encore' red raspberry plant (denoted "7" in FIG. 5 for NY7) and the size of fruit of a 'Taylor' red raspberry plant and shows the fruit of the 'Encore' red raspberry plant are larger in size.

Table 1 below sets forth total fruit yield in kg/ha and average fruit size in grams for 1996–1997 floricane yield at Darrow Farm, located on Gates Road in Geneva, N.Y., for 'Encore,' 'Titan' and 'Taylor' cultivars and for an average of 11 other cultivars in the trial. The test trial was established in 1994 using a randomized complete block diagram. There were five replicates per cultivar. The data of Table 1 are the means of five replicates.

TABLE 1

| | Total fruit yield kg/ha | | | Average fruit size in grams | | |
|---|---|---|---|---|---|---|
| Cultivar | 1996 | 1997 | Average | 1996 | 1997 | Average |
| Titan | 15,061 | 8,928 | 11,955 | 3.11 | 2.78 | 2.95 |
| Encore | 7,326 | 11,309 | 9,318 | 3.03 | 2.80 | 2.92 |
| Taylor | 6,982 | 9,697 | 8,340 | 2.07 | 1.96 | 2.02 |
| Average of 11 other cultivars | 8,912 | 8,986 | 8,949 | 2.72 | 2.13 | 2.43 |

Table 2, below, sets forth total yield in kg/ha and an average fruit size in grams for floricane yield at Robbins Farm, located on Sutton Road in Geneva, N.Y., for the years 1994–1997. This test trial was established in 1990. Data listed in the table are from individual plots unless denoted by parentheses, indicating the number of replicates analyzed that year.

TABLE 2

| Cultivar | 1994 | 1995 | 1996 | 1997 | 94–97 Average |
|---|---|---|---|---|---|
| | Average Fruit Size in Grams/Berry | | | | |
| Encore | 3.10(2) | 2.78(4) | 2.96(3) | 2.80(3) | 2.91 |
| Prelude | — | 2.02 | 2.28 | 2.43 | 2.24 |
| Killarney (unpatented) | — | 2.14 | 2.43 | 1.96 | 2.18 |
| Canby | — | 2.20(2) | 2.15 | 1.98 | 2.11 |
| Sentry (unpatented) | 2.31 | 2.18 | 2.13 | 1.93 | 2.14 |
| | Total Yield in kg/ha | | | | |
| Encore | 7,224(2) | 8,838(4) | 9,247(3) | 7,422(3) | 8,183 |
| Prelude | — | 7,812 | 7,995 | 7,728 | 7,845 |
| Killarney | — | 7,267 | 7,814 | 8,244 | 7,775 |
| Canby | — | 8,153(2) | 11,342 | 3,435 | 7,643 |
| Sentry (unpatented) | 4,110 | 4,675 | 7,796 | 2,369 | 4,738 |

'Prelude' is the subject of a pending U.S. patent application which has been assigned Application Ser. No. 09/166,854.

The average total fruit yield of 'Encore' red raspberry plants at the Darrow Farm trial in 1996–1997 was greater than that from 'Taylor' cultivar but less than that from 'Titan' cultivar, and was greater than the combined average yield of 11 other advanced selections and cultivars in the trial (Table 1, above). The average total fruit yield of 'Encore' red raspberry plants at the Robbins Farm from 1994–1997 was slightly higher than that from 'Killarney' and 'Canby' cultivars (Table 2).

'Encore' red raspberry plants have very good fruit size, averaging 2.9 grams per berry over the entire season from 1994–1997 at the Robbins Farm site (Table 2) and 2.9 grams per berry from 1996–1997 at the Darrow Farm site (Table 1). The average size of fruit from 'Encore' red raspberry plant is much greater than that of fruit from 'Canby,' 'Killarney' and 'Taylor' cultivars and only slightly less than that of fruit from 'Titan' cultivar. 'Encore' red raspberry plants maintained large fruit size over the entire harvest season.

The fruit of 'Encore' red raspberry plants have a pleasant, mild and well balanced flavor and are more attractive and better flavored than fruit of 'Titan' red raspberry plants.

Juice soluble solids (sugars), total acidity and pH values for 'Encore,' 'Taylor' and 'Titan' cultivars and an average of other cultivars are set forth in Table 3, below. Average soluble solids, total acidity, and pH values in Table 3 are from the average of the three years, 1995 to 1997, and minimum and maximum scores are for the total period and are not averages. In Table 3, the superscript "z" indicates the mean of 25 other cultivars tested from 1995 to 1997 and the superscript "y" indicates the mean of 13 other cultivars tested from 1995–1997. In Table 3, "Ave." means average, "Min." means minimum and "Max." means maximum.

TABLE 3

| | Soluble Solids (°Brix) | | | Total Acidity | | | pH | | |
|---|---|---|---|---|---|---|---|---|---|
| Cultivar | Ave. | Min. | Max. | Ave. | Min. | Max. | Ave. | Min. | Max. |
| Encore | 9.9 | 9.0 | 13.4 | 2.05 | 1.55 | 2.30 | 3.13 | 2.95 | 3.35 |
| Taylor | 11.0 | 10.0 | 14.4 | 2.08 | 1.91 | 2.36 | 3.10 | 3.00 | 3.30 |
| Titan | 9.0 | 7.8 | 10.6 | 1.92 | 1.69 | 2.40 | 3.23 | 3.15 | 3.30 |
| All Others | 10.1z | 7.2 | 14.0 | 1.86y | 1.09 | 2.43 | 3.19y | 2.85 | 3.70 |

As indicated in Table 3, 'Encore' fruit have a soluble solids (sugar) level higher than fruit of 'Titan' cultivar and lower than fruit of 'Taylor' cultivar. Other data show that 'Encore' fruit have a soluble solids (sugar) level higher than fruit of 'Killarney' and 'Latham' (unpatented) cultivars and lower than fruit of 'Canby' cultivar. Total acidity of fruit of 'Encore' red raspberry plants is higher than that of fruit of 'Titan' cultivar and lower than that of fruit of 'Taylor' cultivar (Table 3). Other data show that total acidity of fruit of 'Encore' red raspberry plants is higher than that of fruit of 'Canby' cultivar and lower than that of fruit of 'Killarney' cultivar.

Figure 14:
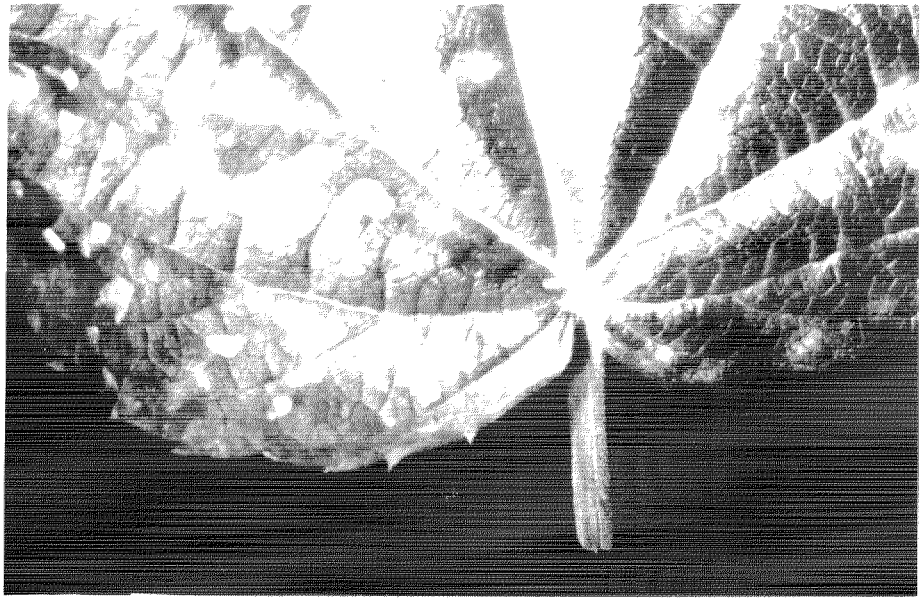
FIG. 14 is a photograph of a leaf of a 'Taylor' red raspberry plant infected with Raspberry Leaf Spot Disease.

'Encore' red raspberry plants have not been noted to be particularly resistant or susceptible to any raspberry pests in the Northeast region. FIG. 14 shows a leaf of a 'Taylor' red raspberry plant infected with raspberry leaf spot disease. 'Encore' red raspberry plants are less susceptible to raspberry leaf spot disease than 'Taylor' red raspberry plants. 'Encore' cultivar is intermediate in its susceptibly to Phytophthora root rot (*P. fragariae* var. *rubi*) 'Encore' cultivar is more resistant to Phytophthora than 'Titan' cultivar but less resistant than 'Latham' cultivar. Proper site selection and use of clean planting stock well help to prevent introduction of the disease. Amending the soil with calcium sulfate prior to planting and/or utilizing raised bed culture can help to minimize the buildup of disease.

Fruit harvest very easily, are dry to the touch, handle easily, and are well suited for wholesale packaging and distribution. 'Encore' cultivar is adapted to u-pick, retail and wholesale markets. Its firm fruit withstand handling and packing to produce an attractive pack for resale.

'Encore' cultivar has been adapted to a wide range of sites. Coarse, well drained soils not previously planted with Rubus are best. Sites with properly managed crop rotations and weed control practices prior to planting provide better conditions for plant establishment. Heavy, fine textured soils with poor drainage are not recommended. 'Encore' cultivar is vigorous and productive on an annual basis as long as weed control and plant nutrition are adequate for optimum plant health.

What is claimed is:

1. A new and distinct raspberry plant, 'Encore,' as herein described and illustrated and identified by the characteristics enumerated above.

* * * * *